United States Patent [19]

Panton et al.

[11] Patent Number: 4,596,144
[45] Date of Patent: Jun. 24, 1986

[54] ACOUSTIC RANGING SYSTEM

[75] Inventors: Stanley Panton, Peterborough; Steven J. Woodward, Port Hope, both of Canada

[73] Assignee: Canadian Corporate Management Co., Ltd., Canada

[21] Appl. No.: 713,751

[22] Filed: Mar. 19, 1985

[30] Foreign Application Priority Data

Sep. 27, 1984 [CA] Canada .................. 464143

[51] Int. Cl.[4] ........................... G01N 29/00
[52] U.S. Cl. ........................ 73/620; 73/290 V
[58] Field of Search ............. 73/290 V, 609, 610, 73/620; 367/99, 908; 364/562

[56] References Cited

U.S. PATENT DOCUMENTS 4,000,650  1/1977  Snyder .................. 73/290 V

Primary Examiner—Stephen A. Kreitman

[57] ABSTRACT

In an acoustic ranging system, an echo signal received following a shot is repeatedly sampled and the samples digitized to produce a statistical data base representing the received echo profile which can be analyzed by various methods to determine the point on the time axis of the profile which corresponds to a wanted echo, and the degree of confidence with which the wanted echo has been identified. The number of shots taken depends upon the conditions at the site being monitored and upon the degree of confidence with which the wanted echo has been determined, and the order in which points in a multipoint system are monitored is determined by an adaptive scanning system which directs shots to different points following a system determined by a predetermined hierarchy, by the results provided by previous shots, by the conditions existing at different points, and by the receipt of outside signals. In order to improve resolution beyond that permitted by the sampling rate selected, the data base produced may be used as an adjunct to an analog determination of the actual elapsed time before receipt of a wanted echo, either by using the data base to determine a temporal "window" within which a wanted echo may be expected, and the expected amplitude of that echo, so that an accurate analog determination of the receipt of a wanted echo becomes possible, or by using the data base to provide an adaptive time variant gain control signal for the echo signal receiver so as to facilitate analog detection of the wanted echo.

21 Claims, 9 Drawing Figures

ACOUSTIC RANGING SYSTEM

This invention relates to a system for the ultrasonic monitoring of levels of particulate solids and liquids, particularly but not exclusively in confined spaces where spurious echoes and high noise levels may exist.

Acoustic ranging systems are widely used for monitoring levels in bins, tanks and silos, and also for measuring flow rates of liquids by sensing the level of the liquid in a narrow spillway. In such systems a burst or "shot" of high frequency sound is projected downwards from a transducer to the surface of the material whose level is being monitored, and the time lapse before reception of a return echo signal from the material surface is determined. The level of the material can then be computed from this time lapse. In practice, problems arise in isolating the return signal from spurious echoes and background noise. Spurious echoes occur because of multiple path reflections off the walls of an enclosure, or reflections from such obstructions as lumps of material adhering to a bin wall or reflective structures within the bin. The desired echo. may be spread out temporally and its amplitude reduced if the surface of the material is sloped or coned, or by splashing or other disturbance of the surface. Background noise levels will be high in spillways, or if a container being monitored is in the course of being filled. Furthermore, the amplitude of the return echo falls off rapidly as the distance from the transducer increases, so that spurious short range echoes and acoustic or electrical noise may have far greater amplitudes than a wanted long range echo.

Conventionally, this last problem has been tackled by using an amplifier for the return signal having a time variant gain, such that the gain of the amplifier increases with the time that has elapsed since a shot so as to compensate for the disadvantage that noise signals also are subjected to progressively increasing amplification with elapsed time, making it in turn progressively more difficult to isolate a desired signal. Examples of systems utilizing amplifiers with time variable gain are disclosed in U.S. Pat. Nos. 4,451,909 (Kodera et al) and 4,386,409 (Petroff).

Another approach to this problem is to subject the signal to logarithmic amplification, such that the gain of the amplifier is dependent on the instantaneous amplitude of the signal. This approach, exemplified in U.S. Pat. No. 4,145,761 issued to Nappin, compresses the dynamic range of the signal and thus somewhat facilitates recognition of significant echo signals without making the treatment of noise signals undesirably time variant. In order to recognize echo signals, the logarithmically amplified signal is differenced with a linear ramp signal. In another ultrasonic level measuring device using logarithmic amplifiers, disclosed in U.S. Pat. No. 3,010,318 (Mongan), a sample of the input signal is also logarithmically amplified and used to cancel errors in the amplified output signal occasioned by amplitude variations in the input.

In yet another approach, the peak detection threshold applied to the received signal is varied with time, as exemplified by U.S. Pat. No. 4,315,325 (Blades) whose U.S. Pat. No. 4,400,976 is also concerned with reducing noise in the received signal.

In order to separate the wanted echo from spurious echoes, quite sophisticated signal processing systems have been proposed. Thus in U.S. Pat. No. 4,386,409, peaks in the received signal are detected, and the data so gathered from each shot is digitized and subjected to digital processing in conjunction with data gathered from further shots with a view to eliminating spurious readings. U.S. Pat. No. 4,210,969 is a further example of a system in which data as to peaks in the received signal is digitized prior to subsequent processing.

Other patents disclosing means for processing received signals in ultrasound ranging systems are U.S. Pat. Nos. 3,889,523 (Nolte) and 4,375,166 (Auphan).

To the best of applicants' knowledge, none of the prior art proposals outlined above provides a wholly successful solution to the problems outlined above in cases where the incidence of background noise and spurious echoes is high, and where a large number of bins, silos or other enclosures or "points" are to be monitored on a continuous basis. Reliability of readings can be improved by taking multiple shots at each point monitored, but this slows down operation, whilst no amount of additional readings will help in cases when it is beyond the resolving power of the system to isolate the correct echo from multiple echoes or background noise.

An object of the present invention is to provide an ultrasonic ranging system which is capable, using a given type of transducer, of achieving improved resolution of received echoes and an improved standard of monitoring.

According to the invention, there is provided improved signal processing means in an acoustic ranging system comprising at least one transducer directed towards the surface of material whose level is to be monitored, a transmitter to energize selectively each transducer whereby to cause it to emit a shot of high frequency sound, and a receiver receiving and amplifying energy from said at least one shot echoed back to said transducer over a subsequent period, the time lapse after a shot before receipt of an echo being proportional to the distance of the origin of the echo. The signal processing means are provided comprising analog to digital converter means to sample repeatedly the output signal from the receiver and to digitize the samples; memory means to store a sequence of digitized samples so produced in respect of at least one shot and form therefrom a digital data base depicting the amplitude/time profile of the received signal; means to utilize the data in said data base to help isolate a point on the time axis of the output signal produced by at least one shot and deemed most probable to correspond to a wanted echo; and means to provide data as to a range represented by said point on the time axis.

Preferably the receiver incorporates a logarithmic amplifier, most preferably a multiple channel logarithmic amplifier. Preferably also the memory means forms the data base either from samples taken from one shot or the average of samples taken from a number of shots. Preferably a scanning system is provided which determines the transducer to which each shot is directed, according both to a predetermined hierarchy and to the result of a previous shot.

The data stored in the data base may be utilized directly to isolate a point on the time axis corresponding to a wanted echo, but in this case the resolution of the system will be limited by the sampling rate utilized, which in turn will be limited by the time required to process the data and the data storage capacity available. In many instances, the readily available resolution will be entirely satisfactory, but where greater resolution is required, the data base may be utilized to provide enhanced analog processing of the output signal from the receiver. In one embodiment, the data base is utilized to define a temporal window within which the wanted echo may be expected, and the expected amplitude of the echo signal, and the analog signal from the receiver during a subsequent shot is then examined during the window to determine the precise instant of occurrence of an echo of the expected amplitude. The advantages of the digital technique are thus combined with the resolution of the analog technique. In another embodiment, the echo profile stored in the data base during an initial shot or shots is filtered to smooth out short term fluctuations, and is utilized to provide a time variant gain control signal to the receiver, thus producing an analog output signal which can be examined to determine the wanted echo. The gain control signal so produced will be derived from the actual time/gain characteristics of the system being monitored and should thus improve the recognition and accurate temporal resolution of the wanted echo.

The invention is described further with reference to the accompanying drawings, in which.

Figure 1:
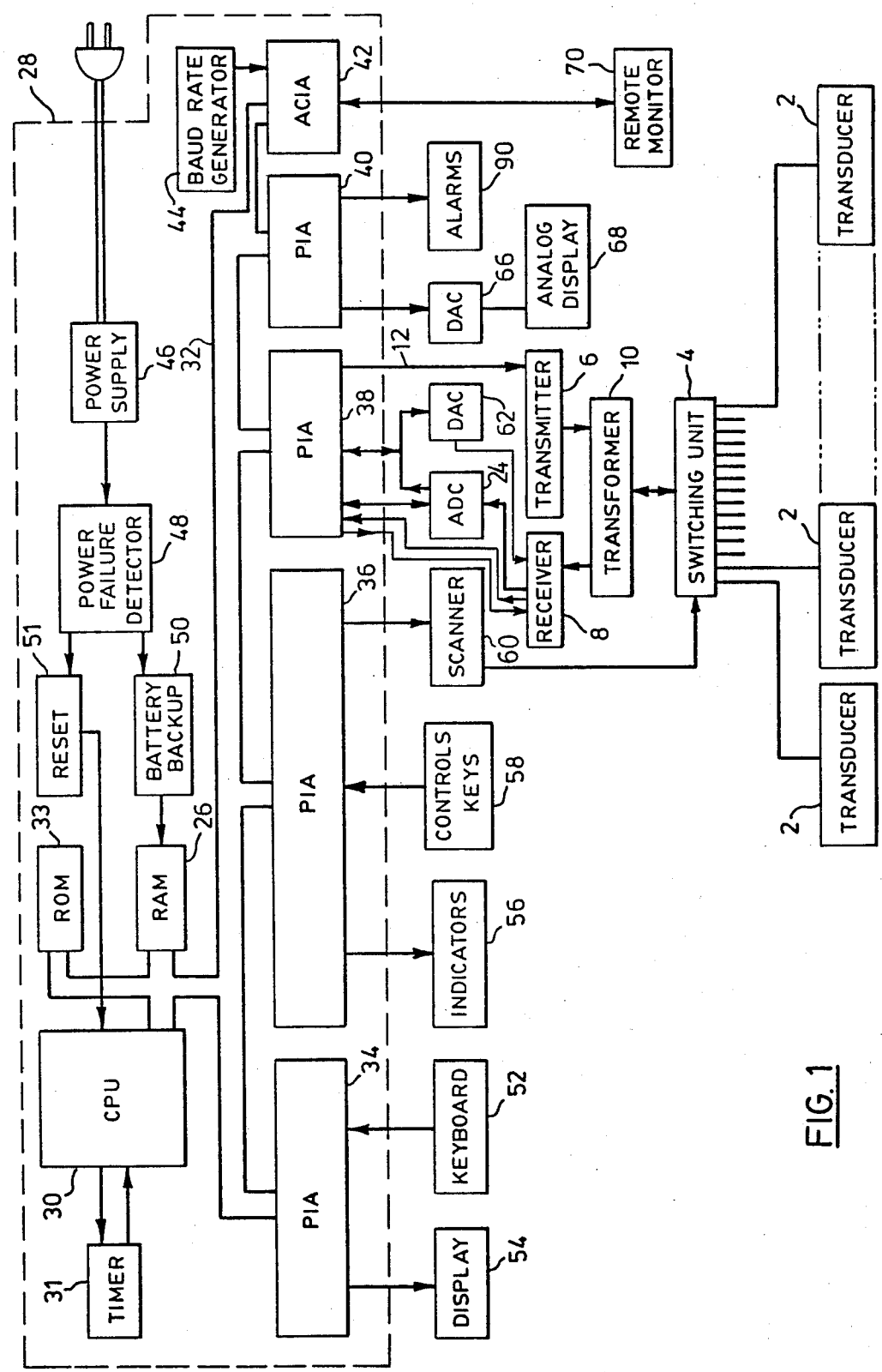
FIG. 1 is a simplified block diagram of a system embodying the invention.

Referring to FIG. 1, there is shown a monitoring system for determining the level of liquids or particulate solids in one or more bins, silos, hoppers or other confined spaces. For the purpose of description it is assumed that the levels of particulate material in a group of silos is being monitored.

Each silo to be monitored is provided at its top end with a downwardly facing acoustic transducer 2. Any transducer conventionally used in acoustic ranging systems may be utilized, although the use of transducers of the type disclosed in U.S. Pat. No. 4,333,028 (Panton) is preferred because of their high efficiency and good directional characteristics. A switching unit 4 comprising a number of relays, controlled as described further below, is used to place individual transducers selectively in connection with a transmitter 6 and a receiver 8 through a transformer 10. The transmitter acts on receipt of a trigger pulse on line 12 to generate a short burst or shot of high frequency energy which is applied via the switching unit to a selected transducer 2. The trigger pulse is used to generate a blanking pulse which disables the receiver 8 during transmission of the shot and for a short time thereafter, during which no wanted echo signal can be expected. When the receiver is enabled, it receives via the transformer 10 electrical signals generated by the transducer 2 in response to signals picked up by the latter, which may be reflections of the transmitted shot, or represent electrical or acoustic noise from extraneous sources.

Thus far the system is conventional, and further description is believed unnecessary. We have found however that by suitable processing of the received signals, and suitable control of the switching unit 10, data as to levels within the silos can be captured more reliably and rapidly. To this end, the receiver 8 provides amplification of the received signal, and alternative embodiments of its internal organization are shown in more detail in FIGS. 2, 3 and 4.

Figure 2:
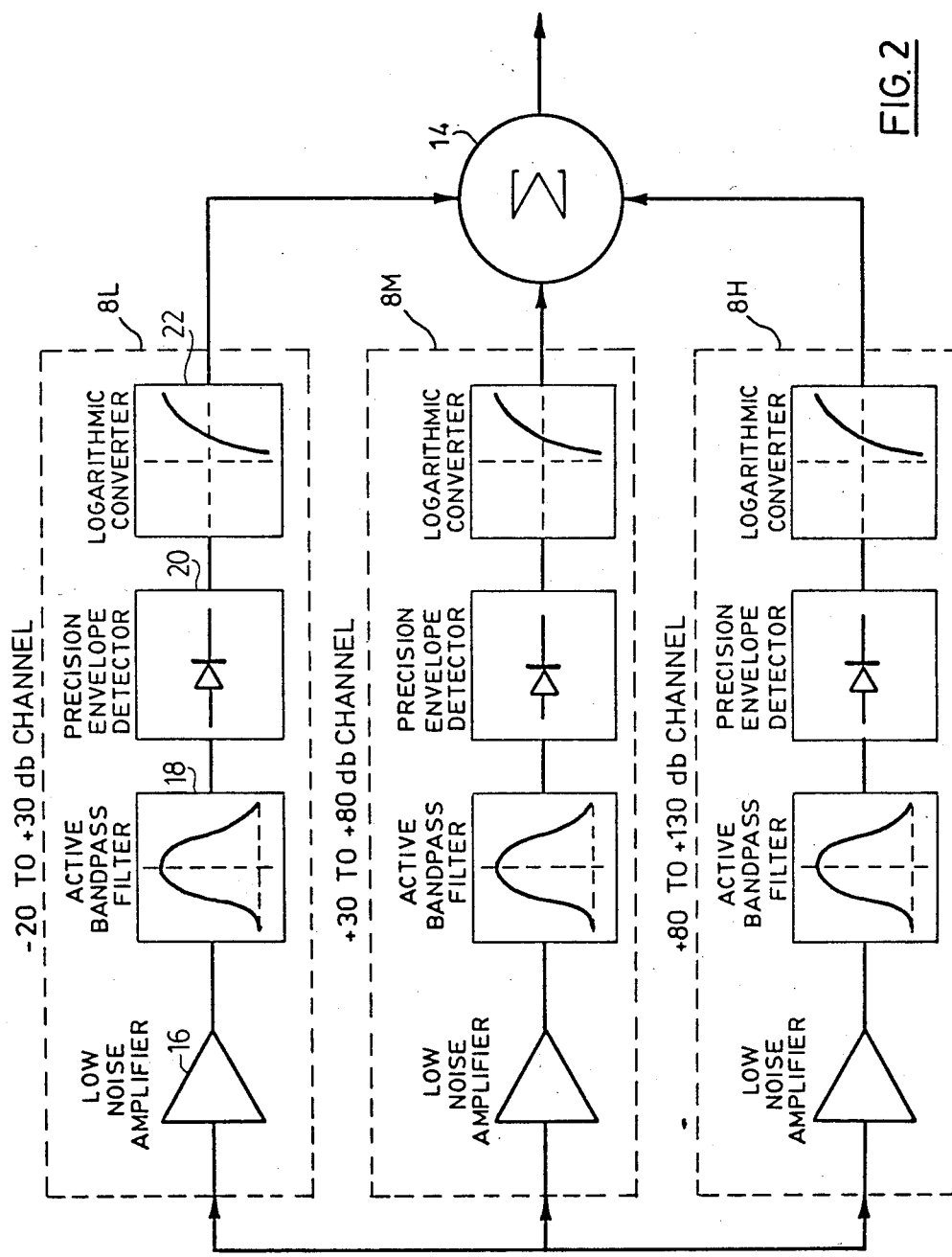
FIG. 2 is a block diagram of one embodiment of receiver unit incorporated in the transceiver shown in FIG. 1.

Referring first to the embodiment of FIG. 2, the input to the receiver is applied to three processing channels 8L, 8M and 8H, the outputs of which are summed in an adder 14. Channel 8L is shown as comprising a low noise input amplifier 16, an active bandpass filter 18 tuned to the transmitter frequency, a precision envelope detector 20, and a logarithmic converter 22 configured to produce a logarithmic response to signals between predetermined thresholds. The other channels may be similar, but with their overall gain and response thresholds adjusted so that the channels respond respectively to signals within adjacent but non-overlapping signal amplitude ranges. The low amplitude signal channel 8L may for example respond to input signals in the amplitude range $-20$ to $+30$ db, the middle amplitude signal channel 8M to input signals in the amplitude range $+30$ db to $+80$ db, and the high amplitude channel to input signals in the amplitude range $+80$ db to $+130$ db, referred to as 1 $\mu$V RMS at the transducer. In practice it may be advantageous to simplify the construction of the channels 8M and 8H, since the applied signal levels will be high enough to render the noise performance of their input amplifiers less critical whilst the threshold of signals processed by channel 8H is such that noise signals should be excluded: this means that the bandpass filter may be omitted without significant loss of performance. The separation of the signal channels through the receiver means that the noise performance of the channel 8L can be improved since its input amplifier operates at fixed gain and requires a smaller dynamic range than would otherwise be the case. Alternatively three channel amplification can be provided by time multiplex operation of a single filter, detector and logarithmic amplifier in conjunction with either separate pre-amplifiers for each channel, or a multiple switchable gain pre-amplifier.

The output signal from the adder 14 of receiver 8 is applied to the input of an analog to digital converter 24 having a sampling rate dependent upon the resolution required for the range measurement. For example, if a level measurement in 5 cm steps is required, a sample repetition rate of about 4000 per second will be required, according to the velocity of sound within the silo, which will vary according to the temperature and composition of the atmosphere therein. The digitized data thus generated is transferred to the random access memory (RAM) 26 of a computer 28.

The computer 28 is of conventional architecture, comprising a central processing unit (CPU) 30, data and address buses, shown combined for the sake of simplicity by the reference numeral 32, read only memory (ROM) 33 providing program storage, random access memory 26, a timer 31, peripheral interface adapters (PIA) 34, 36, 38, 40, providing a number of parallel input and/or output ports and control lines, and an asynchronous communication interface adaptor (ACIA) 42 with an associated baud rate generator 44. Conveniently the major components of the computer are implemented by members of the 6800 microprocessor family, e.g. a 6808 microprocessor, 6821 PIAs and a 6850 ACIA. Buffering and decoding logic has been omitted for the sake of simplicity.

In order to provide protection against power failure, a line operated power supply 46 of the computer 28 (which supply will also normally power the other components shown in FIG. 1) has an associated power failure detector 48, which enables a battery backup supply 50 for the RAM 26, and also operates a reset circuit 51 which ensures that the CPU 30 is reset and re-initialized after a power interruption.

The PIA 34 provides an interface between the CPU, a keyboard 52 for the input of data and commands by an operator, and a display 54 for the output data to the operator, as described more fully below. The PIA 36 outputs data on control lines to various status indicators 56 which supplement the display 54, and inputs data from lines controlled by control keys 58 supplementing the keyboard. It also provides an eight bit parallel output which is decoded by a scanner unit 60 to provide control signals for the switching unit 4. The PIA 38 provides a bidirectional eight bit parallel port which can receive data from the ADC 24 or output data to a digital to analog converter (DAC) 62. It also provides a control line 12 on which is output the trigger pulse which activates the transmitter 6 and gates the receiver 8. Additional control lines (not shown) may be used to switch the ADC 24 and the DAC 62 to service a remote temperature sensor which determines the temperature in the silos. Data received from the sensor may be used to apply a correction factor to compensate for variations in the speed of sound with temperature. Extra output and input lines from PIA 38 to the receiver 8 are utilized in the alternative embodiments described below with reference to FIGS. 3 and 4. The PIA 40 provides a multibit parallel output to a further DAC 66 which provides an isolated high resolution analog output 68 which may be applied by a user to an external controller or other equipment. The output from DAC 62 may be applied to an analog display device such as an oscilloscope, or may, in a further embodiment described below with reference to FIG. 4, be utilized to provide a gain control signal to the receiver 8.

The ACIA 42 provides two way serial communication via a 20 ma current loop or RS232C interface with one or more remote monitors 70, which are typically intelligent terminals having display and keyboard facilities which can duplicate those provided by the display 54 and keyboard 52 thus enabling supervision and control of the system from one or more remote points.

Operation of the system as so far described is most easily considered in two parts, firstly the processing of shots from individual points, and secondly the determination of the destination point of each successive shot.

Under program control, the PIA 36 outputs a byte to the scanner 60 which decodes the byte and switches a selected transducer into connection with the transformer 10. The PIA 38 then outputs a trigger pulse to the transmitter and receiver 6 and 8, resulting in the transmission of a shot and the subsequent reception, logarithmic amplification and digitization of the return echo signal as already described above. Bytes representing the digitized sample are input from ADC 24 through a parallel input port provided by PIA 38 and are stored in memory 26. If the program calls for additional shots at the same transducer 2, as discussed further below, the data recovered from these is stored and averaged or otherwise correlated with the data stored from previous shots. Typically provision is made for separate storage in memory of data from at least three shots. The data stored in memory thus represents the echo profile of a shot or shots and/or the average profile of a series of shots, represented in terms of amplitude in decibels after successive intervals of, typically, 0.25 ms if a 5 cm resolution is required. As compared to prior systems in which echoes are identified and information as to echo location is then digitized, the present system generates a digital data base which can be subjected to any of a wide range of processing algorithms with a view to maximizing likelihood of correctly identifying a wanted echo.

The data so stored is processed under program control using one or more signal processing algorithms embodied in routines stored in ROM 33 designed to detect a wanted echo. The routine selected, and certain parameters utilized thereby, may be changed from default selections, stored in ROM 33 by data entered via keyboard 52.

Figure 5:
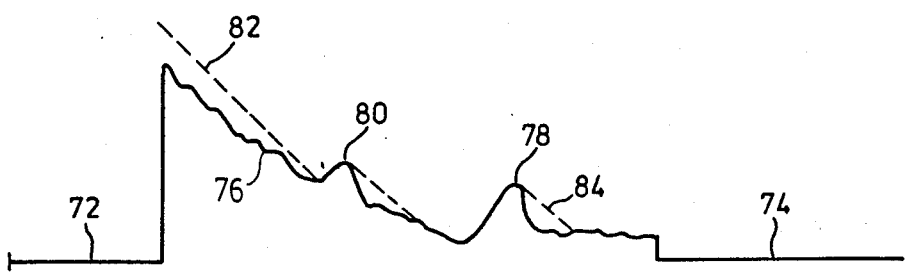
FIGS. 5, 6 and 7 are graphical representations of techniques utilized for processing echo signals.
Figure 6:
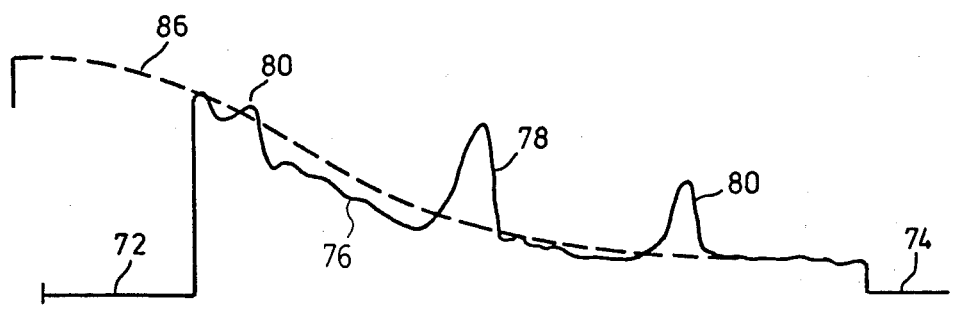
Figure 7:
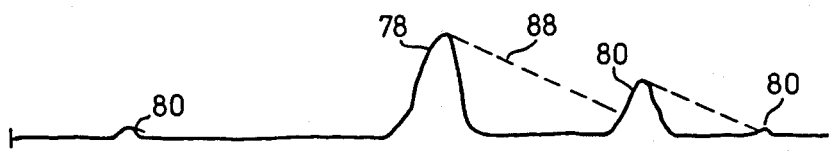

The operation of exemplary processing routines is illustrated in FIGS. 5, 6 and 7. FIGS. 5 and 6 each show the amplitudes of the stored samples relating to an exemplary shot or series of shots presented graphically. Whilst the processing will be described in graphical terms for the sake of clarity, it will be understood that the actual processing is carried out by digital manipulation of the data using conventional techniques. So as to exclude certain spurious signals and to reduce the amount of data to be processed, early samples which may include spurious signals due to ringing of the transducer are excluded (near blanking, as shown at 72), as are late samples (a blanking, as shown at 74) which would correspond to levels below the bottom of the silo were they true echoes. The echo profiles 76 shown in FIGS. 5 and 6 in each case show a true echo 78 and one or more spurious echoes 80.

In FIG. 5, a straight line 82 having a predetermined origin and slope is drawn until it intersects the echo profile, the peak of the profile following the intersection is located, and another line 84 having the same slope is drawn until it again intersects the echo profile. This process is repeated until the far blanking 74 is reached. The peak with the largest rise from the intersection is deemed to be the true echo, and the "echo confidence" is the amount by which the rise of this echo exceeds that of the next largest echo. The slope and origin of the line 82 may be adjusted from default values to optimize the success of the procedure in correctly locating true echoes.

In FIG. 6, a smooth curve 86 is matched to the echo profile by smoothing out the short term fluctuations in the return signal to provide a curve whose amplitude approximates to the variation in gain (dB) of the system with time. This TVG (time varying gain) curve is dependent on the echo profile and is recalculated for each processing operation. Variations in attenuation due to changes in temperature, humidity and dust content of the atmosphere are thus automatically compensated. The TVG curve once derived is subtracted from the original signal profile to leave a series of gain compensated peaks as shown in FIG. 7. A straight line 88 of predetermined slope is then drawn from each peak until it again intersects the echo profile. The echo profile with the largest rise to the peak from the preceding intersection is deemed to be the true echo, the echo confidence being the amount by which this rise exceeds the next largest rise. The slope of the lines 88 may be adjusted to provide optimum discrimination against indirect echoes.

In a variation of the above technique, the area beneath each of the peaks in FIG. 7 is calculated, the largest area being deemed to be associated with the true echo. The echo confidence in this case is deemed to be the margin by which the largest area exceeds the next largest area.

In an endeavour to maximize the opportunities for deriving valid echoes whilst minimizing the elapsed time between successive monitorings of any silo within an installation, the computer is programmed to select the transducers (by means of the bytes applied to scanner 60) according to a predetermined hierarchy. Typically, first priority is given to user requests for a new reading from a particular silo, entered through a monitor 70, second priority to a similar request entered at the keyboard 52, third priority and fourth priority to requests from the same sources for the status of a particular silo when the data stored in respect of the silo is more than a predetermined age, for example two minutes, fifth priority to any silo in respect of which no reading has been taken for more than a predetermined time, for example 60 minutes, sixth priority to any silo whose available data is considered of reduced validity due to its being filled, due to inability on a preceding occasion to obtain a valid echo, or due to known problems in obtaining valid readings, where no reading has been taken for a predetermined period, for example two minutes. Priority is given finally to the silo having the oldest reading. Taking into account this hierarchy, the scanning program follows the flow diagram set forth in FIG. 8, which is believed self explanatory.

In the event of readings from any silo reaching danger level, or repeated failure to obtain valid echoes from a silo (for example as timed out using a lost echo timer implemented using a timer 31 associated with the CPU 30 implemented in software), an appropriate alarm 90 may be activated via PIA 40.

Moreover, by using the DAC 62 and an analog display to reproduce an echo profile using data summoned from memory by commands entered through keyboard 52, it may be possible for an operator to identify a true echo by inspection. A more important function of the DAC 62 and display, in conjunction with the ability of the apparatus to store in memory the profiles of both the current shot and a few preceding shots, is to facilitate the setting up and adjustment of the transducers 2 since the effect of adjustments can be viewed and the profiles of shots taken before and after adjustment can be compared.

In order to determine whether signals from a particular point are subject to raised noise levels, most usually occasioned by filling of a storage container being monitored, the receiver 8 may be enabled when a point is selected, and prior to transmitting a shot, in order to receive a noise signal from that point. If the noise level is above a predetermined threshold, that point is deemed to have special status, for example that of a container being filled. Since a container which is being filled or emptied will exhibit a changing reading, it may be desired in any case to accord it a higher priority than those points exhibiting a static indication. However, an emptying operation in particular may not be accompanied by an enhanced noise level. Thus some external means of indicating a filling or emptying condition may be preferred, in which case the necessary signals may be input to the computer 28 by any convenient means, for example via the remote monitor 70, or an extra channel associated with the scanner 60.

Figure 8:
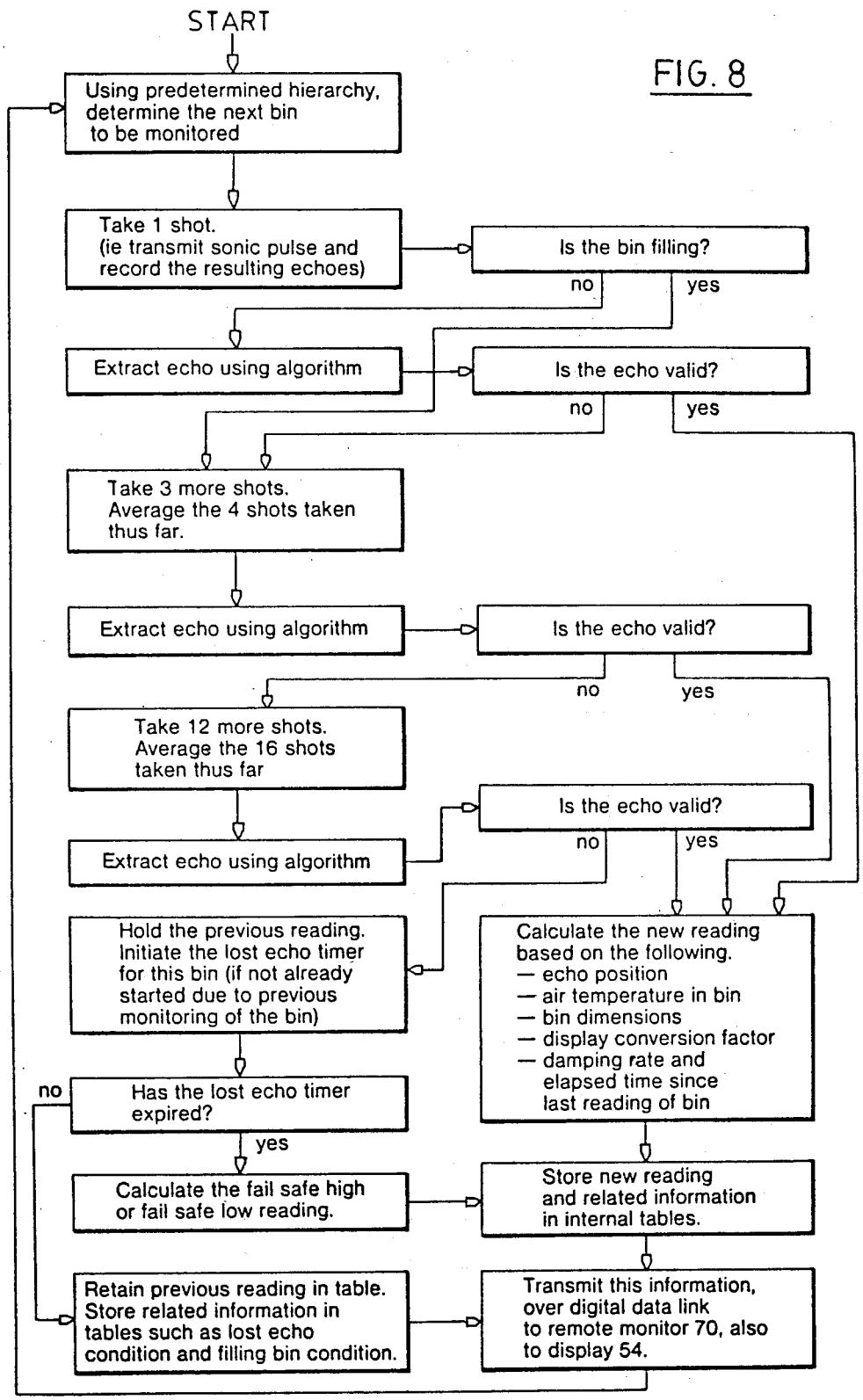
FIG. 8 is a flow diagram illustrating one mode of scanning plural vessels to determine the level therein.

It is believed that in the light of the functional description given above and the flow diagram of FIG. 8, a detailed listing of the programming of the computer 28 is unnecessary. The code utilized will be highly dependent upon the actual microprocessor chip and support chips utilized and can be readily implemented by those familiar with programming techniques for such chips or by reference to standard textbooks describing such techniques.

Figure 3:
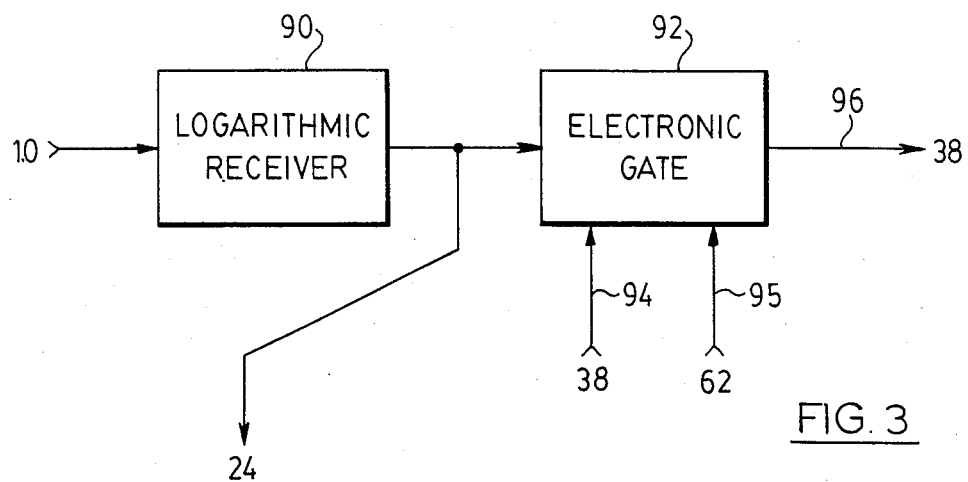
FIG. 3 is a block diagram of an alternative embodiment of receiver unit incorporated in the transceiver shown in FIG. 1.
Figure 9:
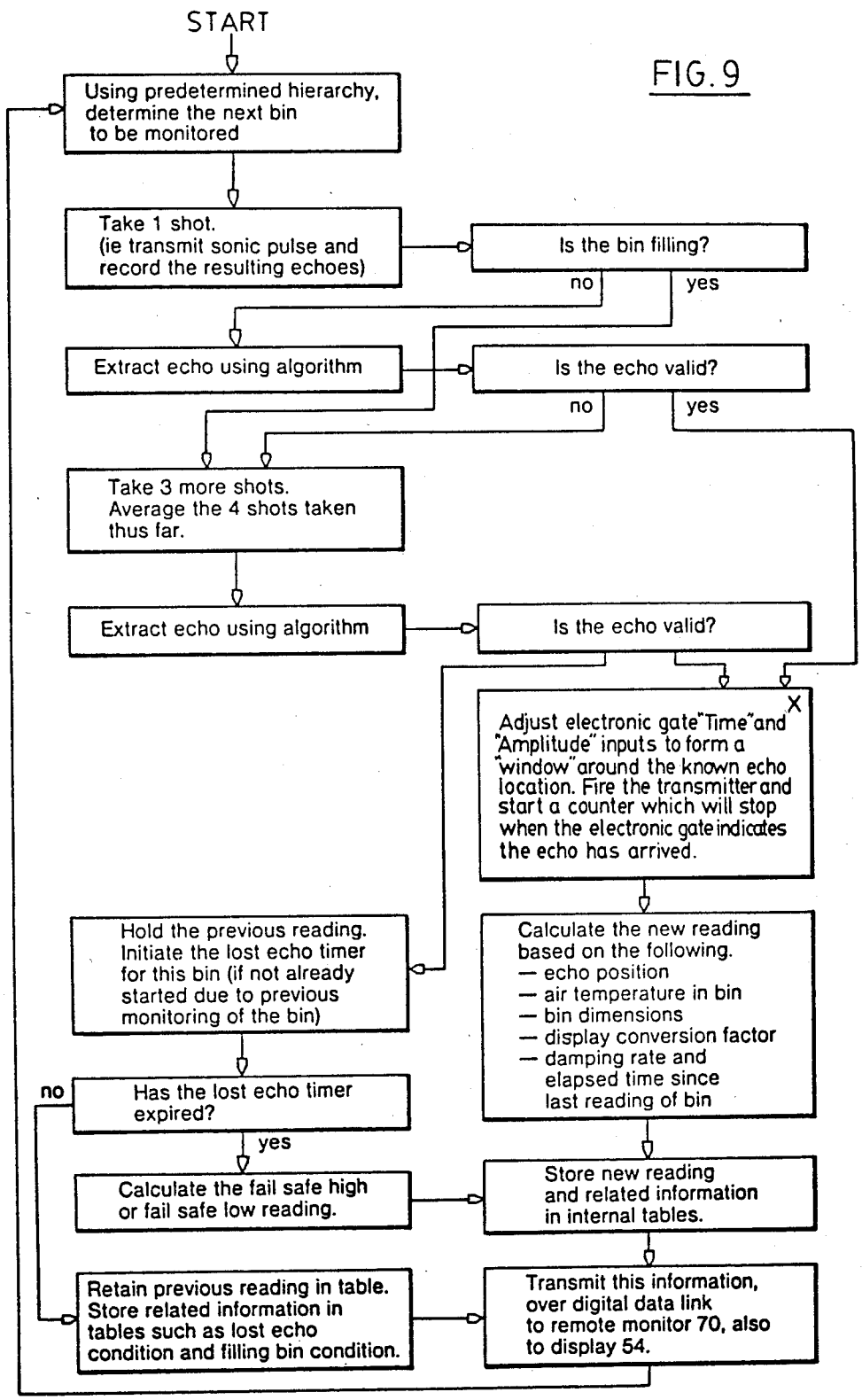
FIG. 9 is a flow diagram illustrating a modified mode of scanning plural vessels to determine levels therein.

Referring now the embodiment of which the receiver 8 is shown in FIG. 3 (the remainder of the apparatus being constructed as shown and described with reference to FIG. 1, although there are differences in function), it is found in some instances that it is not practical to obtain sufficient resolution in the range measurement obtained by the previously described embodiment whilst maintaining the sampling rates and memory capacity of the apparatus at levels which can be economically implemented. Resolution can be improved by modifying the receiver 8 as shown in FIG. 3 and somewhat modifying the program utilized as described further in and with reference to FIG. 9. In FIG. 3, the logarithmic receiver 90 may be constructed in exactly the same manner as already described with reference to FIG. 2. Its output however, as well as being transmitted to the computer via the analog/digital converter 24, is also applied to a programmable gating circuit 92. The output transmitted to the computer is processed as already described so as to identify a wanted echo, as well as the temporal location of this echo and its amplitude, to the degree of precision permitted by the sampling rate. The data so developed is used to program the gating circuit 92. On a subsequent shot, data from a preceding shot is utilized to provide firstly an enabling signal on an output line 94, which signal is true over a period commencing shortly before the expected arrival of a wanted echo, based on the measured time of arrival during the preceding shot. The wanted echo amplitude data from the preceding shot is also converted by digital to analog converter 62 and used to set an amplitude threshold via line 95 with which the output of receiver 90 can be compared when the gate 92 is enabled. When the receiver signal reaches this threshold whilst the gate is enabled, a logic signal it transmitted to the computer on line 96, the elapsed time between the transmission of the shot and the receipt of this signal being accurately timed by the timer 31 associated with the CPU 30, regardless of the sampling rate of the analog to digital converter 24. This modified mode of operation is illustrated in the flow diagram of FIG. 9, from which it will be noted that most of the program may remain unaltered.

The physical arrangement described above with reference to FIG. 3 also supports a further mode of operation which can save time in obtaining accurate readings where the wanted echoes are well defined and can readily be distinguished from spurious signals. In this case the signals transmitted to the computer via converter 24 during the initial part of the return signal following a shot are utilized to predict a time varying gain curve, in accordance with which the amplitude signal on line 98 is adjusted to change the threshold of gate 92. The enabling signal on line 94 is delayed until the gain curve has been determined.

Figure 4:
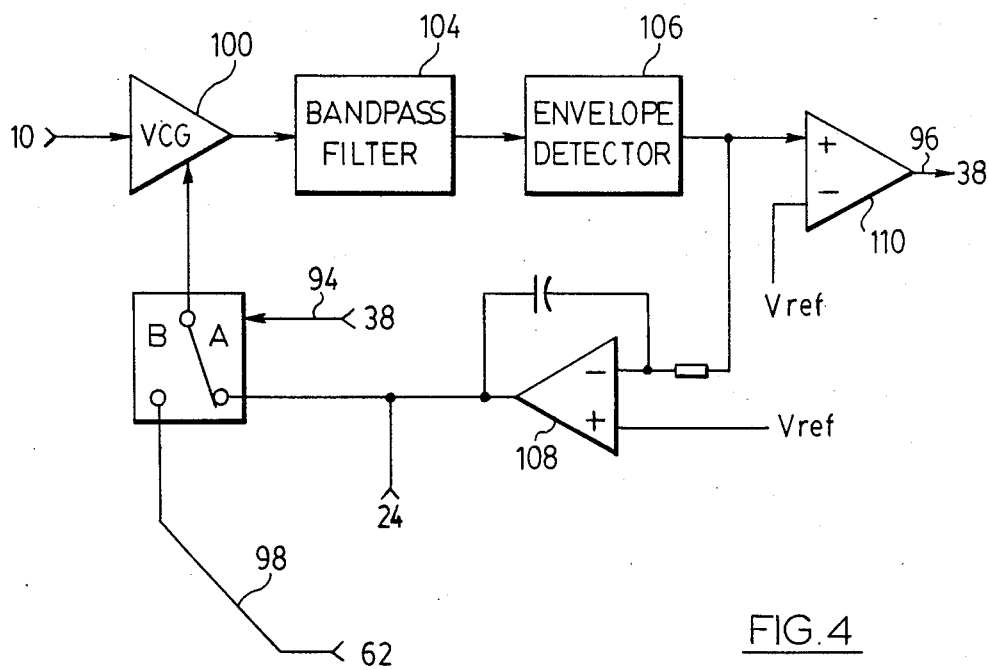
FIG. 4 is a block diagram of a further alternative embodiment of receiver unit incorporated in the transceiver shown in FIG. 1.

In the embodiment of receiver shown in FIG. 4, the input from the transducer is applied to a gain controlled amplifier 100. This amplifier preferably has a logarithmic gain control characteristic, and its gain control signal may be derived from two alternative sources, according to the condition of a switch 102 controlled by line 94 in a manner described further below. The output of amplifier 100 is passed through a bandpass filter 104 and an envelope detector 106 to provide an analog signal. This signal is applied to a fast integrator 108 and in turn is applied to the computer via the analog to digital converter 24 and to the amplifier 100 when the switch 102 is in state A. The data base accumulated by the computer during several shots is filtered to smooth out short term fluctuations and provide a curve representing the gain/time characteristics of the container being modified in the manner described with reference to the curve 86 in FIG. 6, and in subsequent shots digital signals representing this curve are converted to analog signals by converter 62 and applied to the amplifier 100 by applying a signal on line 94 to switch 102 to cause it to assume condition B. The output of detector 106 is applied to a comparator 110, and if a threshold determined by a reference potential is exceeded, a signal is output on line 96 which enables the elapsed time to be accurately determined as in the previous embodiment, without any limit on resolution by the sampling rate of the converter 24. The flow diagram for this embodiment will be the same as FIG. 9 except for the block marked X, whose legend would be amended to read "Derive time-varying gain curve from accumulated data, and control receiver gain according to this curve. Fire the transmitter and start a count which will be terminated when comparator indicates that echo has arrived."

We claim:

1. In an acoustic ranging system comprising at least one transducer directed towards the surface of material whose level is to be determined, a transmitter to energize selectively each said transducer whereby to cause it to emit at least one shot of high frequency sound, and a receiver receiving and amplifying energy from said at least one shot echoed back to said transducer over a subsequent period, the time lapse after a shot before receipt of an echo being proportional to the distance of the origin of the echo, the improvement wherein:
signal processing means are provided comprising analog to digital converter means to sample repeatedly the output amplitude of the signal from the receiver at defined intervals and to digitize the samples; memory means to store an extended sequence of digitized samples so produced in respect of at least one shot and form therefrom a digital data base depicting an amplitude/time profile of the received signal with a resolution dependent on the sampling intervals; means to utilize the amplitude profile depicted by the data in said data base to help isolate relative to a time axis a portion of the output signal produce by at least one shot deemed most probable to correspond to a wanted echo; and means to determine a range represented by an echo within said portion of the time axis.

2. A system according to claim 1, wherein the receiver incorporates an envelope detector and an amplifier receiving the detected signal and having a logarithmic characteristic.

3. A system according to claim 2, wherein the receiver comprises multiple channels, each handling signals within a certain amplitude range.

4. A system according to claim 1, wherein the data utilization means is operative both to determine which of multiple peaks stored echo profile most probably represents a wanted echo, and to quantify that probability.

5. A system according to claim 4, wherein the data utilization means comprises means to determine intersections of the echo profile traced by successive samples with straight lines of predetermined slope which are tangent with peaks in the profile at their origins and intersect the profile at their other ends.

6. A system according to claim 5, in which the data utilization means includes means to determine the greatest amplitude difference between the intersection of a line and the next succeeding peak, that peak being deemed the wanted echo, and the amount by which the greatest amplitude difference exceeds the next greatest amplitude is deemed to represent a degree of confidence that the wanted echo has been identified.

7. A system according to claim 4, wherein the data utilization means provides a procedure for filtering the profile which smooths out short term fluctuations to provide a curve approximating to the variation in gain of the system with elapsed time following a shot, and subtracts this curve from the original profile to provide a residual echo profile prior to analyzing the residual echo profile for identification of a wanted echo.

8. A system according to claim 7, wherein the data utilization means comprises means to determine intersections of the residual echo profile with straight lines of predetermined slope which are tangent with peaks in the profile at their origins and intersect the profile at their other ends.

9. A system according to claim 8, in which the data utilization means includes means to determine the greatest amplitude difference between the intersection of a line and the next succeeding peak, that peak being deemed the wanted echo, and the amount by which the greatest amplitude difference exceeds the next greatest amplitude is deemed to represent a degree of confidence that the wanted echo has been identified.

10. A system according to claim 7, wherein the utilization means comprises means to determine the areas beneath peaks in the residual echo profile, the peak associated with the largest such area being deemed the wanted echo, and the amount by which this area exceeds the next largest such area being deemed to represent a degree of confidence that the wanted echo has been identified.

11. A system according to claim 4, wherein the signal processing means is operative to initiate repetition of a shot where the probability that the wanted echo has been correctly determined by the utilization means falls below a predetermined threshold.

12. A system according to claim 11, including means to determine whether output signals received from each transducer may be sugject to higher than normal noise levels, and means responsive to said determination means to require repeated shots in a storage means determined to be subject to higher than normal noise levels.

13. A system according to claim 12, wherein the determination means are operative to determine whether a storage means being monitored is being filled.

14. A system according to claim 1, further comprising means to gate the output signal from the receiver during a shot to provide a time window including said point on the time axis corresponding to the wanted signal, and means to detect an echo occurring within that window whereby to provide a determination of the time of arrival of said echo independent of the sampling rate of the digital to analog converter.

15. A system according to claim 14, wherein the signal utilization means is operative to determine the amplitude of the wanted echo from the data in said data base, and including means to set an echo detection threshold in said echo detection means responsive to said amplitude.

16. A system according to claim 1, wherein said utilization means filters the data in said data base to produce an amplitude/time profile of the received signal free of short term fluctuations and substantially representing the gain/time profile of the system in which said at least one shot is being taken, wherein said receiver includes a gain controlled amplifier to which said amplitude/time profile is applied as a gain control signal, and wherein a means to detect an echo are provided to receive the output of said receiver to provide a determination of the time of arrival of an echo independent of the sampling rate of the digital to analog converter.

17. A system according to claim 16, wherein said data base is built up using at least one shot, and said receiver is gain controlled and its output detected during a subsequent shot.

18. A system according to claim 1, including a threshold detector to detect an echo in the output signal from the receiver, independent of the sampling rate of the digital to analog converter, and wherein said utilization means filters the data stored in said data base during at least the initial portion of the output signal of the receiver to smooth out short term fluctuations and produce an extrapolated gain/time profile of system, the threshold of said detector being determined by the instantaneous amplitude of said profile.

19. A system according to claim 1, having transducers located at several points, and further including scanning means connecting any one of said transducers to said transmitter and receiver, said scanning means being operative to select transducers according to a priority hierarchy in which the priority of a point in the absence of outside commands is dependent at least in part upon the relative history of previous shots applied to the several points.

20. A system according to claim 19, configured to provide higher priority to points expected to provide changing or unreliable readings.

21. A system according to claim 20, configured to provide higher priority to points at which signals from the associated transducer are subject to enhanced noise levels.

* * * * *

UNITED STATES PATENT AND TRADEMARK OFFICE
CERTIFICATE OF CORRECTION

PATENT NO. : 4,596,144

DATED : June 24, 1986

INVENTOR(S) : Panton et al.

It is certified that error appears in the above-identified patent and that said Letters Patent is hereby corrected as shown below:

Column 10, line 67, "said" should read --a--.

Signed and Sealed this

Twentieth Day of July, 1993

Attest:

MICHAEL K. KIRK

*Attesting Officer*  *Acting Commissioner of Patents and Trademarks*

US004596144B1

REEXAMINATION CERTIFICATE (2690th)

United States Patent [19]
Panton et al.

[11] B1 4,596,144
[45] Certificate Issued Oct. 10, 1995

[54] ACOUSIC RANGING SYSTEM

[75] Inventors: Stanley Panton, Peterborough; Steven J. Woodward, Port Hope, both of Canada

[73] Assignee: Milltronics Ltd., Peterborough, Canada

Reexamination Request
No. 90/003,584, Sep. 30, 1994
No. 90/003,771, Mar. 28, 1995

Reexamination Certificate for:
Patent No.: 4,596,144
Issued: Jun. 24, 1986
Appl. No.: 713,751
Filed: Mar. 19, 1985

Certificate of Correction issued Jul. 20, 1993.

[30] Foreign Application Priority Data

Sep. 27, 1984 [CA] Canada ................................ 464143

[51] Int. Cl.$^6$ ........................ G01N 29/00; G01F 23/28
[52] U.S. Cl. .................................... 73/620; 73/290 V
[58] Field of Search .............................. 73/290 V, 609, 73/610, 620; 367/99, 908; 364/562

[56] References Cited

U.S. PATENT DOCUMENTS

| | | |
|---|---|---|
| 2,746,480 | 5/1956 | Hildyard . |
| 2,753,542 | 6/1956 | Rod et al. ........................ 367/108 X |
| 2,755,455 | 6/1956 | Gordon, Jr. . |
| 2,757,354 | 6/1956 | Bolzmann . |
| 2,775,748 | 12/1956 | Rod et al. ........................ 367/108 X |
| 2,780,795 | 2/1957 | Ambrosio . |
| 2,810,860 | 10/1957 | Mork . |
| 2,838,752 | 6/1958 | Philpott . |
| 2,943,296 | 6/1960 | Fryklund . |
| 2,960,678 | 11/1960 | Beard et al. . |
| 3,084,331 | 4/1963 | Dudley . |
| 3,102,261 | 8/1963 | Wippert . |
| 3,115,615 | 12/1963 | Saper . |
| 3,119,091 | 1/1964 | Hopkin et al. . |
| 3,181,157 | 4/1965 | Martin et al. . |
| 3,184,969 | 5/1965 | Bolton . |
| 3,195,103 | 7/1965 | Drenkelfort . |
| 3,212,338 | 10/1965 | O'Maley . |
| 3,214,754 | 10/1965 | Hildebrandt . |
| 3,229,245 | 1/1966 | Hurdle et al. . |
| 3,233,964 | 3/1966 | Stadlin . |
| 3,264,645 | 8/1966 | Hotz ........................ 343/17.1 |
| 3,296,580 | 1/1967 | Hopkin . |
| 3,296,862 | 1/1967 | Ziniuk . |
| 3,314,045 | 4/1967 | Williamson et al. . |
| 3,317,828 | 5/1967 | Schuls . |
| 3,357,246 | 12/1967 | Stearn et al. . |
| 3,380,018 | 4/1968 | Littrell et al. ........................ 340/3 |
| 3,394,589 | 7/1968 | Tomioka . |
| 3,416,127 | 12/1968 | Menin et al. . |
| 3,422,435 | 1/1969 | Cragon et al. . |
| 3,428,939 | 2/1969 | Witt . |
| 3,449,710 | 6/1969 | Moss, Jr. . |
| 3,454,922 | 7/1969 | Dory . |

(List continued on next page.)

OTHER PUBLICATIONS

Donar: A Computer Processing System To Extend Ultrasonic Pulse–Echo Testing (Jul. 1973) (ADC/computer/Fixed Echo Correction) pp. 165–173.

"Implementing Random Logic With Microprocessors" 1973 Institute of Electrical and Electronics Engineering, IEEE Mar. 1973 cover sheet 1 page.

"LSI Building Blocks For Parallel Digital Processors," George Reyling, Jr., National Semiconductor Corporation, 2900 Semiconductor Drive, Santa Clara, California 92051 21/3 p. 1.

"Microprocessor Interfacing Techniques," Rodnayzaks, Austin Lesea, Third Edition, Copyright 1977–79, Sybex, Inc. pp. 16–17.

"Industrial Design With Microcomputers," Steven K. Roberts, Prentice–Hall, Inc., Englewood Cliffs, New Jersey 07632, Copyright 1982 by Steven K. Roberts p. 15.

"Modern Electronic Circuits Reference Manual," John Markus, McGraw–Hill Book Company, New York, New York, Copyright 1980 p. 499.

Baggeroer, A. B., "Tapped Delay Line Models for the Dereverberation of Deep Water Multiples," 1973. pp. 33–54.

Blecki, D. J., "Trapping Transients Digitally," *Electronic Products*, vol. 15, No. 12, May 21, 1973, pp. 211–219.

Cashin, P. M. et al., "A Novel Method for Analysing Singly–Occurring Pulses with Nanosecond Resolution," *The Radio and Electronic Engineer*, vol. 38, No. 1, Jul. 1969, pp. 13–16.

Eastwood, E., "Radar Engineering: Progress and Prospect," Inaugural Address from *Proceedings of the Institute of Electrical Engineers*, vol. 120, No. 1, Jan. 1973, pp. 1–12.

(List continued on next page.)

*Primary Examiner*—Thomas P. Noland

[57] ABSTRACT

In an acoustic ranging system, an echo signal received following a shot is repeatedly sampled and the samples digitized to produce a statistical data base representing the received echo profile which can be analyzed by various methods to determine the point on the time axis of the profile which corresponds to a wanted echo and the degree of confidence with which the wanted echo, has been identified. The number of shots taken depends upon the conditions at the site being monitored and upon the degree of confidence with which the wanted echo has been determined, and the order in which points in a multipoint system are monitored is determined by an adaptive scanning system which directs shots to different points following a system determined by a predetermined hierarchy, by the results provided by previous shots, by the conditions existing at different points, and by the receipt of outside signals. In order to improve resolution beyond that permitted by the sampling rate selected, the data base produced may be used as an adjunct to an analog determination of the actual elapsed time before receipt of a wanted echo, either by using the data base to determine a temporal "window" within which a wanted echo may be expected, and the expected amplitude of that echo, so that an accurate analog determination of the receipt of a wanted echo becomes possible, or by using the data base to provide an adaptive time variant gain control signal for the echo signal receiver so as to facilitate analog detection of the wanted echo.

U.S. PATENT DOCUMENTS

| | | |
|---|---|---|
| 3,456,715 | 7/1969 | Freedman et al. |
| 3,460,059 | 8/1969 | Purnhagen |
| 3,469,261 | 9/1969 | Lambert, Jr. et al. |
| 3,478,308 | 11/1969 | Stanley et al. |
| 3,486,377 | 12/1969 | Franchi |
| 3,486,381 | 12/1969 | Farese |
| 3,491,333 | 1/1970 | Goulet et al. |
| 3,505,637 | 4/1970 | Abruzzo ................................. 340/3 |
| 3,520,186 | 7/1970 | Adams et al. |
| 3,539,978 | 11/1970 | Stedtnitz |
| 3,540,275 | 11/1970 | Post et al. |
| 3,555,498 | 1/1971 | Nye et al. |
| 3,564,490 | 2/1971 | Camp |
| 3,582,872 | 6/1971 | Prager |
| 3,588,795 | 6/1971 | Linardos et al. |
| 3,589,196 | 6/1971 | Van Dyck et al. ............. 73/290 V X |
| 3,624,596 | 11/1971 | Dickenson et al. |
| 3,631,483 | 12/1971 | Ruggles et al. |
| 3,656,134 | 4/1972 | Brown |
| 3,660,841 | 5/1972 | Powers et al. |
| 3,673,553 | 6/1972 | Miura et al. |
| 3,673,554 | 6/1972 | McAlpin |
| 3,680,088 | 7/1972 | Bryant et al. |
| 3,683,324 | 8/1972 | Hoxsie |
| 3,696,326 | 10/1972 | McAlpin |
| 3,696,384 | 10/1972 | Lester |
| 3,710,310 | 1/1973 | Moss, Jr. et al. |
| 3,723,960 | 3/1973 | Harris |
| 3,727,178 | 4/1973 | Stedtnitz |
| 3,733,582 | 5/1973 | Eck et al. |
| 3,739,325 | 6/1973 | Ludwig |
| 3,742,438 | 6/1973 | Brede et al. |
| 3,745,829 | 7/1973 | Franchi ........................... 73/290 V |
| 3,757,285 | 9/1973 | Ferré |
| 3,787,802 | 1/1974 | Brahman |
| 3,787,803 | 1/1974 | Beebe |
| 3,790,925 | 2/1974 | Ahrens |
| 3,834,233 | 9/1974 | Willis et al. ................... 73/290 V |
| 3,884,074 | 5/1975 | Robertsson .................... 73/290 V |
| 3,896,411 | 7/1975 | Mackey et al. |
| 3,899,668 | 8/1975 | Tucker, Jr. |
| 3,921,122 | 11/1975 | Christoff |
| 3,924,258 | 12/1975 | Fowler |
| 3,944,963 | 3/1976 | Hively |
| 3,944,965 | 3/1976 | Caporin et al. |
| 3,965,983 | 6/1976 | Watson ............................ 166/250 |
| 3,985,030 | 10/1976 | Charlton ......................... 73/290 V |
| 3,996,798 | 12/1976 | Vander Heyden .............. 73/195 |
| 4,000,650 | 1/1977 | Snyder ............................. 73/290 |
| 4,044,606 | 8/1977 | Le Blanc et al. |
| 4,107,685 | 8/1978 | Martin et al. ................ 367/105 X |
| 4,130,018 | 12/1978 | Adams et al. .................. 73/290 V |
| 4,145,741 | 3/1979 | Nappin ........................... 73/602 X |
| 4,146,869 | 3/1979 | Snyder ........................ 73/290 V X |
| 4,167,753 | 9/1979 | Lynk ................................ 358/140 |
| 4,202,049 | 5/1980 | Wetzel ............................. 367/96 |
| 4,204,280 | 5/1980 | Slaton ............................. 367/95 |
| 4,210,969 | 7/1980 | Massa ........................ 73/290 V X |
| 4,245,332 | 1/1981 | Schaefer ......................... 367/98 |
| 4,259,734 | 3/1981 | Harmel ........................... 367/101 |
| 4,274,148 | 6/1981 | van't Hullenaar ............. 367/122 |
| 4,312,053 | 1/1982 | Lipsky ............................ 367/127 |
| 4,322,827 | 3/1982 | Weber ............................. 367/99 |
| 4,352,167 | 9/1982 | Hashimoto et al. ........... 367/127 |
| 4,357,672 | 11/1982 | Howells et al. ................ 364/561 |
| 4,398,423 | 8/1983 | Takahashi ....................... 73/631 |
| 4,402,231 | 9/1983 | Ryan .............................. 73/861.27 |
| 4,420,824 | 12/1983 | Weber ............................. 367/908 |
| 4,487,065 | 12/1984 | Carlin et al. ................... 73/290 V |
| 4,630,226 | 12/1986 | Tanaka ............................ 364/561 |
| 4,637,463 | 1/1987 | McCoy ........................... 367/908 X |
| 4,679,175 | 7/1987 | Eder et al. ..................... 367/99 X |
| 4,700,569 | 10/1987 | Michalski et al. ............. 73/290 V |
| 4,719,605 | 1/1988 | Eder et al. ..................... 367/99 X |
| 4,959,817 | 9/1990 | Murphree ....................... 367/97 |
| 4,961,174 | 10/1990 | Teel et al. ...................... 367/97 |
| 4,969,131 | 11/1990 | Harris, Jr. ..................... 367/99 X |
| 4,972,386 | 11/1990 | Lan ................................. 367/99 |

OTHER PUBLICATIONS

Echard, J. D. et al., "Digital Filtering for Radar Signal Processing Applications," *IEEE Transactions on Audio and Electroacoustics*, vol. AU–20, No. 1, Mar. 1972, pp. 42–52.

Kan, E. P. F. et al., "Randomly Sampled Digital Filters," *IEEE Transactions on Audio and Electroacoustics*, vol. AU–20, No. 1, Mar. 1972, pp. 52–57.

Maginness G., & Kay L., "Ultrasonic Imaging in Solids," *The Radio and Electronic Engineer*, vol. 41, No. 2, Feb. 1971, pp. 91–93.

Moyer, M. W., et al., "Expanding the Capability of a Laboratory Ultrasonic Testing Facility," *Materials Evaluation*, Oct. 1973, pp. 193–198.

Nelson, G. A., et al., "High–Speed Octave Band Digital Filtering," *IEEE Transactions on Audio and Electroacoustics*, vol. AU–20, No. 1, Mar., 1972, pp. 58–65.

Parry, H. Dean, et al., "The Design and Operation of an Acoustic Radar," *IEEE Transactions on Geoscience Electronics*, vol. GE–10, No. 1, Jan. 1972, pp. 58–64.

Seydel, J. A., et al., "A Computer–Processed Ultrasonic Pulse–Echo NDT System," *Materials Evaluation*, Nov. 1973, pp. 223–228.

Shreeve, K. H., et al., "A Weather Radar Video Integrator and Processor," *IEEE Transactions on Geoscience ELectronics*, vol. GE–6, No. 3, Aug. 1968, pp. 152–155.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINTED THAT:

The patentability of claims 1–21 is confirmed.

* * * * *